(12) United States Patent
Shimada et al.

(10) Patent No.: US 12,097,100 B2
(45) Date of Patent: Sep. 24, 2024

(54) METHOD FOR PRODUCING ABSORBENT BODY

(71) Applicant: ZUIKO CORPORATION, Settu (JP)

(72) Inventors: Takahiro Shimada, Settu (JP); Daisuke Furukawa, Settu (JP)

(73) Assignee: ZUIKO CORPORATION, Settu (JP)

( * ) Notice: Subject to any disclaimer, the term of this patent is extended or adjusted under 35 U.S.C. 154(b) by 16 days.

(21) Appl. No.: 17/619,390

(22) PCT Filed: Jul. 2, 2020

(86) PCT No.: PCT/JP2020/025983
§ 371 (c)(1),
(2) Date: Dec. 15, 2021

(87) PCT Pub. No.: WO2021/002420
PCT Pub. Date: Jan. 7, 2021

(65) Prior Publication Data
US 2022/0395405 A1 Dec. 15, 2022

(30) Foreign Application Priority Data
Jul. 3, 2019 (JP) ................. 2019-124824

(51) Int. Cl.
*A61F 13/15* (2006.01)
*B05B 13/02* (2006.01)

(52) U.S. Cl.
CPC .. *A61F 13/15764* (2013.01); *A61F 13/15658* (2013.01); *B05B 13/0207* (2013.01)

(58) Field of Classification Search
None
See application file for complete search history.

(56) References Cited

U.S. PATENT DOCUMENTS 9,235,884 B2 * 1/2016 Ogasawara ........... G06T 7/0008
2008/0038504 A1   2/2008 Manabe et al.
(Continued)

FOREIGN PATENT DOCUMENTS

CN    108608689 A  * 10/2018  ....... A61F 13/15658
JP    S63-283777 A    11/1988
(Continued)

OTHER PUBLICATIONS

PCT/ISA/210, "International Search Report for International Application No. PCT/JP2020/025983," Oct. 6, 2020.

*Primary Examiner* — Barbara J Musser
(74) *Attorney, Agent, or Firm* — HAUPTMAN HAM, LLP

(57) ABSTRACT

An absorbent body in which a larger amount of a granular absorbent substance penetrates into the inside of a fiber sheet is produced. A fiber sheet having napped one main surface is supplied to a conveying device and conveyed while the other main surface of the fiber sheet is being sucked through a conveyance surface. A granular absorbent substance is sprayed onto the napped one main surface of the fiber sheet to cause the substance to penetrate into the inside of the fiber sheet in a suction section. A pressure difference increasing device is provided that faces the one main surface of the fiber sheet sprayed with the absorbent substance and being conveyed in the suction section, and that suppresses air from flowing through the fiber sheet inward from the conveyance surface to increase the pressure difference between the conveyance surface side and the opposite side of the fiber sheet.

11 Claims, 7 Drawing Sheets

(56) References Cited

U.S. PATENT DOCUMENTS

2013/0284362 A1 10/2013 Tsujimoto et al.
2019/0029890 A1 1/2019 Nakamura et al.

FOREIGN PATENT DOCUMENTS

| JP | 2002-650 A | 1/2002 |
| JP | 2006-149453 A | 6/2006 |
| JP | 2008-154605 A | 7/2006 |
| JP | 2007-521869 A | 8/2007 |
| WO | 2005/072671 A1 | 8/2005 |
| WO | 2012/108330 A1 | 8/2012 |
| WO | 2017/131014 A1 | 8/2017 |

* cited by examiner (a)

(b)

(a)

(b)

METHOD FOR PRODUCING ABSORBENT BODY

RELATED APPLICATIONS

The present application is National Phase of International Application No. PCT/JP2020/025983 filed Jul. 2, 2020, and claim priority from Japanese Application No. 2019-124824, filed Jul. 3, 2019, the disclosures of which are hereby incorporated by reference herein in its entirety.

TECHNICAL FIELD

The present invention relates to an absorbent body producing method and an absorbent article, and more specifically, related to a technology of producing an absorbent body in which an absorbent substance is disposed inside a fiber sheet.

BACKGROUND ART

An absorbent body used for absorbent articles such as disposable diapers, disposable shorts, sanitary napkins and incontinence pads contains a granular absorbent substance capable of absorbing and holding liquid.

This absorbent body is produced, for example, by using an absorbent body producing apparatus 101 shown in FIG. 7. As shown in FIG. 7, one main surface side of a fiber sheet 201 being conveyed is napped by a napping device 130. Then, by using a spraying device 140, a granular absorbent substance is sprayed onto the napped one main surface of the fiber sheet 201 while the other main surface of the fiber sheet 201 is supported with a planar conveyance surface, and by using a sucking device 150, the other main surface of the fiber sheet 201 is sucked through the conveyance surface to hold the sprayed absorbent substance on the fiber sheet 201. Then, a cover sheet 202 having a larger width than the fiber sheet 201 is laminated on the one main surface of the fiber sheet 201. Then, by using a folding device 160, the part of the cover sheet 202 protruding from the fiber sheet 201 is folded and overlaid on the other main surface of the fiber sheet 201. Then, by using a crimping device 170, the fiber sheet 201 and the cover sheet 202 are compressed in the lamination direction.

CITATION LIST

Patent Literature

[Patent Literature 1] WO 2017/131014

SUMMARY OF THE INVENTION

Problem to be Solved by the Invention

The continuous absorbent body produced in this way is cut into pieces, and disposed in appropriate positions of an absorbent article. However, rewet readily occurs in a state where the sprayed absorbent substance remains in the vicinity of the surface of the fiber sheet 201. Rewet is less likely to occur when the absorbent substance penetrates into the inside of the fiber sheet.

In view of such circumstances, a problem to be solved by the present invention is to provide an absorbent body producing method with which it is possible to produce an absorbent body in which a larger amount of granular absorbent substance is caused to penetrate into the inside of a fiber sheet from napped one main surface of the fiber sheet and rewet is less likely to occur, and an absorbent article including the absorbent body.

Means for Solving the Problem

To solve the above-mentioned problem, the present invention provides an absorbent body producing method structured as follows:

The absorbent body producing method is provided with (i) a first step in which a fiber sheet having one main surface side thereof napped is supplied to a conveying device and conveyed while an other main surface side of the fiber sheet is being sucked through a conveyance surface of the conveying device, and (ii) a second step in which a granular absorbent substance capable of absorbing and holding liquid is sprayed onto the napped one main surface of the fiber sheet and the sprayed absorbent substance is caused to penetrate into the inside of the fiber sheet in a suction section where the other main surface side of the fiber sheet is sucked through the conveyance surface. At the first and second steps, pressure difference increasing means is provided that faces the one main surface of the fiber sheet sprayed with the absorbent substance and being conveyed in the suction section and that suppresses an air flow penetrating the fiber sheet to move inward from the conveyance surface to thereby increase the pressure difference between the conveyance surface side and the opposite side of the fiber sheet.

According to the above-described method, compared with when no pressure difference increasing means is provided, the pressure difference between the conveyance surface side and the opposite side of the fiber sheet is large, so that the force can be increased by which the absorbent substance sprayed onto the one main surface of the fiber sheet is sucked toward the other main surface side of the fiber sheet. By doing this, the absorbent body can be produced in which a larger amount of granular absorbent substance is caused to penetrate into the inside of the fiber sheet from the napped one main surface of the fiber sheet and rewet is less likely to occur.

A breathable sheet may be laminated on the other main surface side of the fiber sheet. For example, the fiber sheet and the breathable sheet may be supplied to the conveying device in such a manner that the breathable sheet is laminated on the other main surface side of the fiber sheet, or a fiber sheet where the breathable sheet is previously laminated on the other main surface side may be supplied to the conveying device.

Preferably, the pressure difference increasing means is a plate-like or belt-like member having one main surface and an other main surface facing each other. The one main surface of the member faces the one main surface of the fiber sheet sprayed with the absorbent substance and being conveyed in the suction section.

In this case, the air flow penetrating the fiber sheet to move inward from the conveyance surface can be suppressed with a simple structure.

The plate-like or belt-like member may be either in contact with the one main surface of the fiber sheet or separate from the one main surface of the fiber sheet. When the plate-like or belt-like member is in contact with the one main surface of the fiber sheet, it is preferable for the plate-like or belt-like member to move together with the fiber sheet while being in contact with the one main surface of the fiber sheet.

Preferably, in the member, an opening is formed on the one main surface of the member, and an airflow passage communicating with the opening is formed.

In this case, the condition of the airflow penetrating the fiber sheet to move inward from the conveyance surface can be adjusted by the airflow passage.

Preferably, the airflow passage is a through hole passing through between the one main surface and the other main surface of the member, and a plurality of the through holes are formed on the member.

In this case, with a simple structure, the air flow penetrating the fiber sheet to move inward from the conveyance surface can be suppressed.

Preferably, the absorbent body producing method is further provided with (iii) a third step in which an adhesive is applied to one main surface of a cover sheet; and (iv) a fourth step in which the one main surface of the cover sheet where the adhesive is applied is overlaid on the one main surface of the fiber sheet sprayed with the absorbent substance to laminate the cover sheet on the fiber sheet.

In this case, since the adhesive is not directly applied to the fiber sheet sprayed with the absorbent substance, a larger amount of absorbent substance can be caused to penetrate into the inside of the fiber sheet. That is, if the adhesive is applied to the one main surface of the fiber sheet and the absorbent substance is sprayed thereonto, the absorbent substance is bonded by the adhesive, whereby the amount of absorbent substance penetrating into the inside of the fiber sheet is reduced. Compared with this, when the adhesive is not directly applied to the fiber sheet, a larger amount of absorbent substance can be caused to penetrate into the inside of the fiber sheet.

Moreover, the present invention provides an absorbent article structured as follows:

The absorbent article includes the absorbent body produced by any of the above-described absorbent body producing methods, the one main surface of the fiber sheet is disposed on a skin surface side, and the other main surface of the fiber sheet is disposed on a non-skin surface side.

In the absorbent body produced by any of the above-described absorbent body producing methods, by causing a larger amount of absorbent substance to penetrate into the inside of the fiber sheet, the amount of absorbent substance disposed on the one main surface side of the fiber sheet can be made small. Although a large mount of absorbent substance disposed on the skin surface side gives a rough touch, the rough touch can be suppressed because the amount of absorbent substance disposed on the skin surface side can be made small.

Effects of the Invention

According to the present invention, an absorbent body can be produced in which a larger amount of granular absorbent substance is caused to penetrate into the inside of the fiber sheet from the napped one main surface of the fiber sheet and rewet is less likely to occur.

MODE FOR CARRYING OUT THE INVENTION

Hereinafter, embodiments of the present invention will be described with reference to the drawings.

Figure 1:
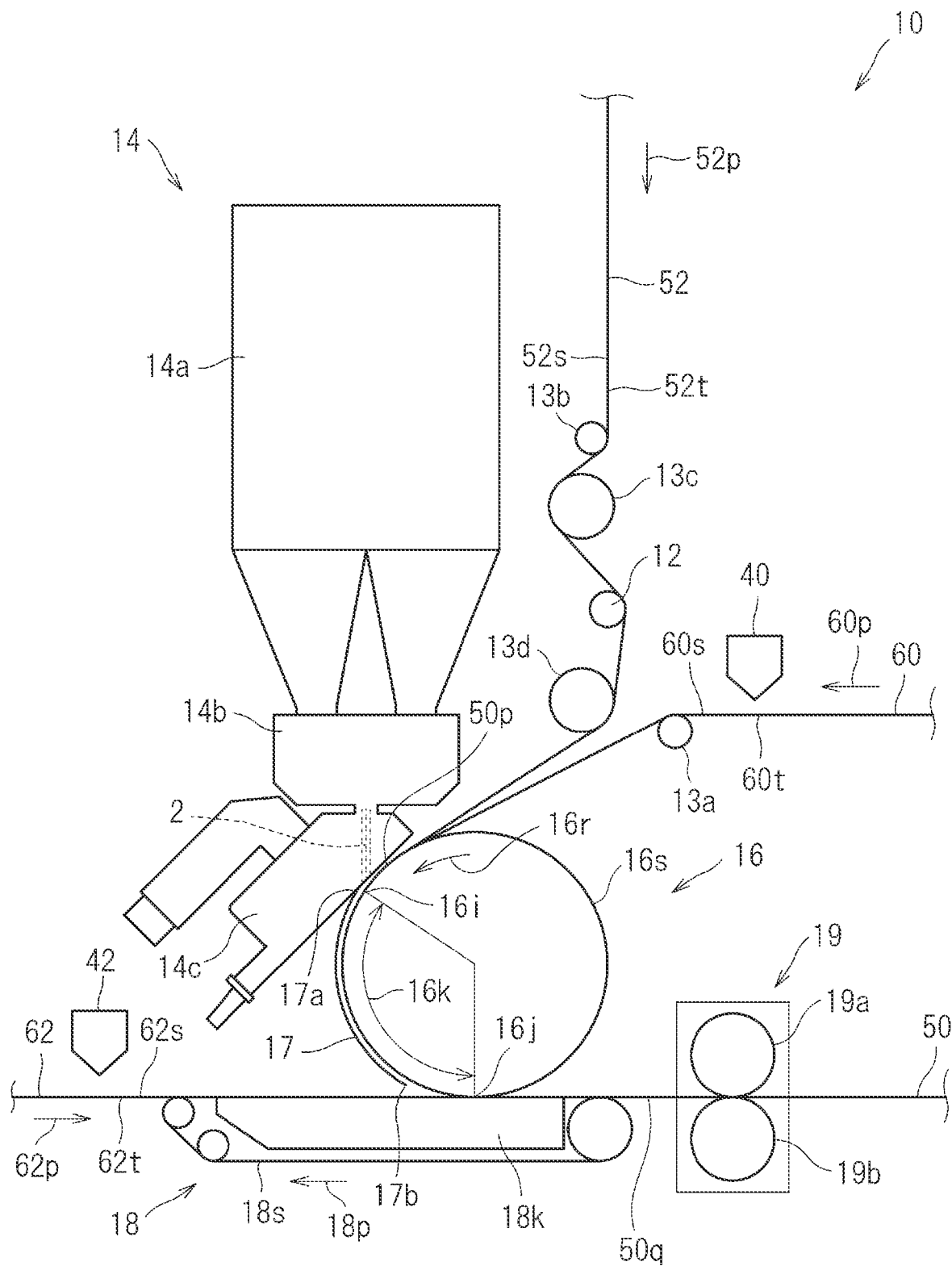
FIG. 1 is a schematic view of an absorbent body producing apparatus (first embodiment).
Figure 2:
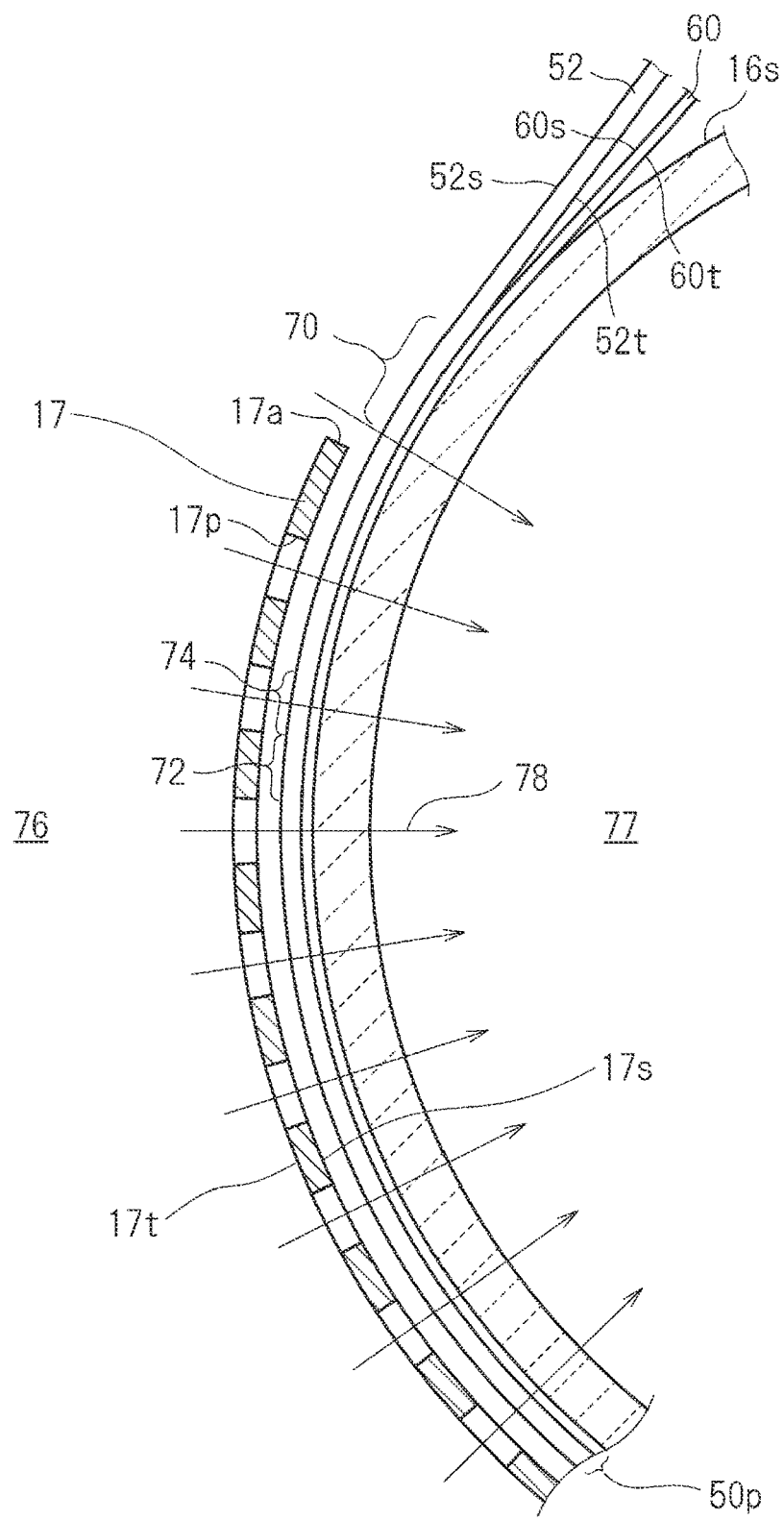
FIG. 2 is a relevant part enlarged view of the absorbent body producing apparatus (first embodiment).
Figure 3:
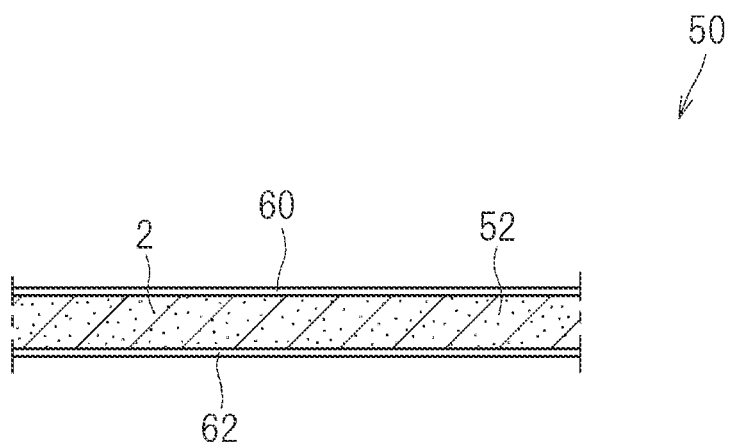
FIGS. 3A and 3B are schematic views of an absorbent body (first embodiment).
Figure 3:
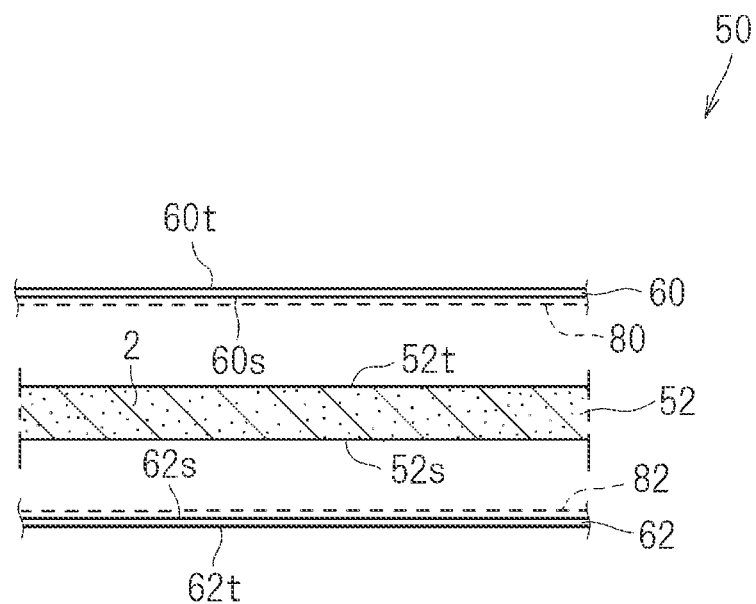

<First embodiment> An absorbent body producing method of a first embodiment will be described with reference to FIGS. 1 to 3B. FIG. 1 is a schematic view of an absorbent body producing apparatus 10 used in the first embodiment. FIG. 2 is a relevant part enlarged view of the absorbent body producing apparatus 10. FIGS. 3A and 3B are schematic views of an absorbent body 50 cut vertically to a conveyance direction. FIG. 3A is an assembled view, and FIG. 3B is a disassembled view.

As shown in FIG. 1, in the absorbent body producing apparatus 10, after a breathable continuous base sheet 60 and fiber sheet 52 supplied to a first conveying device 16 and a continuous cover sheet 62 supplied to a second conveying device 18 are overlaid on each other, they are compressed in the thickness direction by a compressing device 19 and before the cover sheet 62 is overlaid thereon, a granular absorbent substance 2 capable of absorbing and holding liquid is sprayed from a spraying device 14 onto one main surface 52s of the fiber sheet 52 previously napped by a napping device 12, thereby continuously producing the absorbent body 50. The absorbent substance 2 is, for example, SAP (super absorbent polymer).

In the first conveying device 16, a breathable cylindrical conveyance surface 16s having a mesh structure or the like rotates in the direction indicated by the arrow 16r, and the base sheet 60 is wound on the conveyance surface 16s. The first conveying device 16 has inside a space (vacuum chamber) being negative in pressure, and air is sucked inward from the conveyance surface 16s through the conveyance surface 16s in a section 16k (hereinafter, referred to as suction section 16k) between a first position 16i where the base sheet 60 has moved by a predetermined distance after being wound and a second position 16j where the base sheet 60 separates from the conveyance surface 16s.

The base sheet 60 is conveyed in the direction indicated by the arrow 60p, and a first adhesive 80 such as hot melt adhesive (see FIG. 3B) is applied to one main surface 60s thereof by a first applying device 40 in such a manner that the breathability is maintained. Then, after passing a guide roll 13a, the base sheet 60 is supplied to the first conveying device 16 so that the other main surface 60t thereof is in contact with the conveyance surface 16s of the first conveying device 16 (see FIG. 2), and is wound on the conveyance surface 16s of the first conveying device 16. The base sheet 60 is sucked through the conveyance surface 16s in the suction section 16k, and moves together with the conveyance surface 16s. The base sheet 60 is, for example, a sheet of tissue paper.

The fiber sheet 52 is conveyed in the direction indicated by the arrow 52p, is wound on the napping device 12 by guide rollers 13b to 13d, and has one main surface 52s side thereof napped by the napping device 12. Then, the fiber sheet 52 is supplied to the first conveying device 16 in such a manner that the other main surface 52t is overlaid on the one main surface 60s of the base sheet 60 wound on the conveyance surface 16s of the first conveying device 16 (see FIG. 2), a first lamination body 50p where the fiber sheet 52 is laminated on the base sheet 60 is formed, and the fiber sheet 52 moves together with the base sheet 60. The fiber sheet 52 is, for example, an air-through nonwoven fabric. The napping device 12 is, for example, a tiller in which a plurality of blade edges scratch the one main surface 52s of the fiber sheet 52 to nap the one main surface 52s side so as to be bulky. The napping device 12 is unnecessary when the fiber sheet 52 having the one main surface 52s side thereof previously napped is used.

The spraying device 14 sprays the absorbent substance 2 onto the napped one main surface 52s of the fiber sheet 52 of the first lamination body 50p. The absorbent substance 2 is sprayed onto a spray area 70 (see FIG. 2) on the upstream side in the conveyance direction of the first position 16i where suction is started. The spraying device 14 sprays the absorbent substance 2 onto the one main surface 52s of the fiber sheet 52, for example, by mixing a plurality of kinds of absorbent substances stored in a storage 14a by a mixing device 14b and discharging the mixed absorbent substance 2 from a non-illustrated spray port of an opening and closing device 14c. The opening and closing device 14c opens and closes the spray port to thereby spray the absorbent substance 2 intermittently, that is, in such a manner as to continue at intervals in the conveyance direction of the fiber sheet 52.

A member 17 in the form of a plate (hereinafter, referred to as plate-like member 17) is disposed so as to face, with a space in between, the one main surface 52s of the fiber sheet 52 of the first lamination body 50p sprayed with the absorbent substance 2 and being conveyed in the suction section 16k. One end 17a of the plate-like member 17 adjoins the non-illustrated spray port of the spraying device 14, and the other end 17b of the plate-like member 17 adjoins the second conveying device 18.

In the second conveying device 18, a breathable endless belt 18s having a mesh structure or the like circulates in the direction indicated by the arrow 18p, and a vacuum box 18k is disposed inside of the endless belt 18s.

The cover sheet 62 is conveyed in the direction indicated by the arrow 62p, and a second adhesive 82 such as hot melt adhesive (see FIG. 3B) is applied to one main surface 62s thereof by a second applying device 42; then, the cover sheet 62 is supplied to the second conveying device 18 in such a manner that the other main surface 62t is in contact with the endless belt 18s of the second conveying device 18, and moves together with the endless belt 18s while being sucked through the endless belt 18s. The cover sheet 62 is, for example, a sheet of tissue paper.

The first conveying device 16 and the second conveying device 18 are disposed close to each other, and the one main surface 52s of the fiber sheet 52 of the first lamination body 50p being conveyed by the first conveying device 16 is overlaid on the one main surface 62s, sprayed with the second adhesive 82 (see FIG. 3B), of the cover sheet 62 being conveyed by the second conveying device 18, whereby a second lamination body 50q where the cover sheet 62 is laminated on the first lamination body 50p is formed.

The second lamination body 50q, that is, the laminated base sheet 60, fiber sheet 52 and cover sheet 62 pass between a pair of rolls 19a and 19b of the compressing device 19 to be compressed in the thickness direction, so that the first adhesive 80 (see FIG. 3B) applied to the base sheet 60 and the second adhesive 82 (see FIG. 3B) applied to the cover sheet 62 diffuse into the fiber sheet 52 of the second lamination body 50q. This forms the continuous absorbent body 50 where the absorbent substance 2 inside the fiber sheet 52 is fixed. Although not shown, the continuous absorbent body 50 is conveyed to a post-process to be cut into pieces, and then, disposed in appropriate positions of an absorbent article.

A first lamination body 50p where the base sheet 60 and the fiber sheet 52 are previously overlaid on each other may be supplied to the first conveying device 16. Moreover, an absorbent body including no base sheet 60 may be produced by supplying only the fiber sheet 52 to the first conveying device 16. Further, it is possible to produce an absorbent body without the use of the compressing device 19.

Next, the plate-like member 17 will be further described. As shown in FIG. 2, one main surface 17s of the plate-like member 17 faces, with a space in between, the one main surface 52s of the fiber sheet 52 of the first lamination body 50p sprayed with the absorbent substance 2 and being conveyed in the suction section 16k. The plate-like member 17 has a plurality of through holes 17p passing through between the main surfaces 17s and 17t. Since the base sheet 60 is sucked through the conveyance surface 16s, as indicated by the arrows 78, the air flow is caused that passes through the through holes 17p of the plate-like member 17 and penetrates the fiber sheet 52 to move inward from the conveyance surface 16s.

Compared with when no plate-like member 17 is provided, in a second facing area 74 facing the through holes 17p of the plate-like member 17, the air flow is high in flow speed until it impinges on the one main surface 52s of the fiber sheet 52, and high in dynamic pressure on the one main surface 52s side of the fiber sheet 52. For this reason, compared with when no plate-like member 17 is provided, the difference in pressure, that is, the difference in dynamic pressure is large between the conveyance surface 16s side (in FIG. 2, the area indicated by reference numeral 76) and the opposite side (in FIG. 2, the area indicated by reference numeral 77) of the fiber sheet 52.

That is, the plate-like member 17 is pressure difference increasing means that faces the one main surface 52s of the fiber sheet 52 sprayed with the absorbent substance 2 and being conveyed in the suction section 16k and that suppresses the air flow penetrating the fiber sheet 52 to move inward from the conveyance surface 16s to thereby increase the pressure difference between the conveyance surface side 76 and the opposite side 77 of the fiber sheet 52

The provision of the plate-like member 17 makes it possible to enhance the air flow passing through the fiber sheet 52 to move toward the conveyance surface 16s to increase the force by which the granular absorbent substance 2 sprayed onto the one main surface 52s of the fiber sheet 52 is sucked toward the other main surface 52t of the fiber sheet 52.

Moreover, it is possible to make the air flow weak in a first facing area 72 facing the part of the plate-like member 17 where no through holes 17p are formed and make the air flow strong in the second facing area 74 facing the through holes 17p of the plate-like member 17. In this case, the fiber sheet 52 passes the first facing area 72 where the air flow is weak and the second facing area 74 where the air flow is strong, so that shaking of each fiber of the fiber sheet 52 becomes fierce and changes in the flow direction and strength of the air become drastic inside the fiber sheet 52. For this reason, the absorbent substance 2 sprayed onto the one main surface 52s of the fiber sheet 52 is readily released even if entangled with the fibers of the fiber sheet 52, so that it easily moves inside the fiber sheet 52 toward the other main surface 52t of the fiber sheet 52.

Consequently, the absorbent body 50 can be produced in which a larger amount of granular absorbent substance 2 is caused to penetrate into the inside of the fiber sheet 52 from the napped one main surface 52s of the fiber sheet 52 and rewet is less likely to occur.

The through holes 17p of the plate-like member 17 are airflow passages communicating with openings formed on the one main surface of the plate-like member 17. While forming the through holes 17p on the plate-like member 17 simplifies the structure, the airflow passages may be other than the through holes 17p. For example, airflow passages communicating with openings formed on the one main surface 17s of the plate-like member 17 and openings formed on a surface other than the main surfaces 17s and 17t of the plate-like member 17 (for example, the outer peripheral surface) may be formed on the plate-like member 17.

The pressure difference increasing means can be structured without the provision of the airflow passages on the plate-like member 17. For example, by disposing at intervals a plurality of plate members with no airflow passages so as to face the one main surface 52s of the fiber sheet 52 sprayed with the absorbent substance 2 and being conveyed in the suction section 16k, the plate members suppress the air flow penetrating the fiber sheet 52 to move inward from the conveyance surface 16s, so that the pressure difference between the conveyance surface 16s side and the opposite side of the fiber sheet 52 can be made large in the areas adjoining the areas facing the plate members.

In the absorbent body 50, as shown in FIGS. 3A and 3B, the one main surface 60s of the base sheet 60 and the other main surface 52t of the fiber sheet 52 are bonded together by the first adhesive 80. The one main surface 62s of the cover sheet 62 and the one main surface 52s of the fiber sheet 52 are bonded together by the second adhesive 82. Inside the fiber sheet 52, the absorbent substance 2 is disposed. While it is preferable to use the same adhesive as the first and second adhesives 80 and 82, adhesives different in ingredients may be used.

When the absorbent body 50 is used for the absorbent article, it is preferable to form the absorbent article as follows: The one main surface 52s of the fiber sheet 52 is disposed on the skin surface side (that is, the side close to the user's skin in a state where the absorbent article is being used) and the other main surface 52t of the fiber sheet 52 is disposed on the non-skin surface side (that is, the side farther from the user's skin in a state where the absorbent article is being used).

In the absorbent body 50, as mentioned previously, a larger amount of absorbent substance 2 sprayed onto the napped one main surface 52s of the fiber sheet 52 can be caused to penetrate into the inside of the fiber sheet 52. For this reason, the amount of absorbent substance 2 disposed on the one main surface 52s side of the fiber sheet 52 can be made small. Although a large mount of absorbent substance 2 disposed on the skin surface side gives a rough touch, the rough touch can be suppressed because the amount of absorbent substance 2 disposed on the skin surface side can be made small.

An absorbent body producing method of the first embodiment for producing the absorbent body 50 by using the absorbent body producing apparatus 10 described above is provided with at least the following first and second steps, preferably, is provided with the following third and fourth steps:

(i) At the first step, the fiber sheet 52 having the one main surface 52s side thereof napped is supplied to the first conveying device 16 and conveyed while the other main surface 52t side of the fiber sheet 52 is sucked through the conveyance surface 16s of the first conveying device 16. (ii) At the second step, the granular absorbent substance 2 capable of absorbing and holding liquid is sprayed onto the napped one main surface 52s of the fiber sheet 52, and the sprayed absorbent substance 2 is caused to penetrate into the inside of the fiber sheet 52 in the suction section 16k where the other main surface 52t side of the fiber sheet 52 is sucked through the conveyance surface 16s. At the first and second steps, the pressure difference increasing means 17 is provided that faces the one main surface 52s of the fiber sheet 52 sprayed with the absorbent substance 2 and being conveyed in the suction section 16k and that suppresses the air flow penetrating the fiber sheet 52 to move inward from the conveyance surface 16s to thereby increase the pressure difference between the conveyance surface 16s side and the opposite side of the fiber sheet 52.

(iii) At the third step, the adhesive 82 is applied to the one main surface 62s of the cover sheet 62. (iv) At the fourth steps, the one main surface 62s of the cover sheet 62 where the adhesive 82 is applied is overlaid on the one main surface 52s of the fiber sheet 52 sprayed with the absorbent substance 2, and the cover sheet 62 is laminated on the fiber sheet 52.

By the above-described method, it is possible to produce the absorbent body 50 in which a larger amount of granular absorbent substance 2 can be caused to penetrate into the inside of the fiber sheet 52 from the napped one main surface 52s of the fiber sheet 52 and rewet is less likely to occur.

Figure 4:
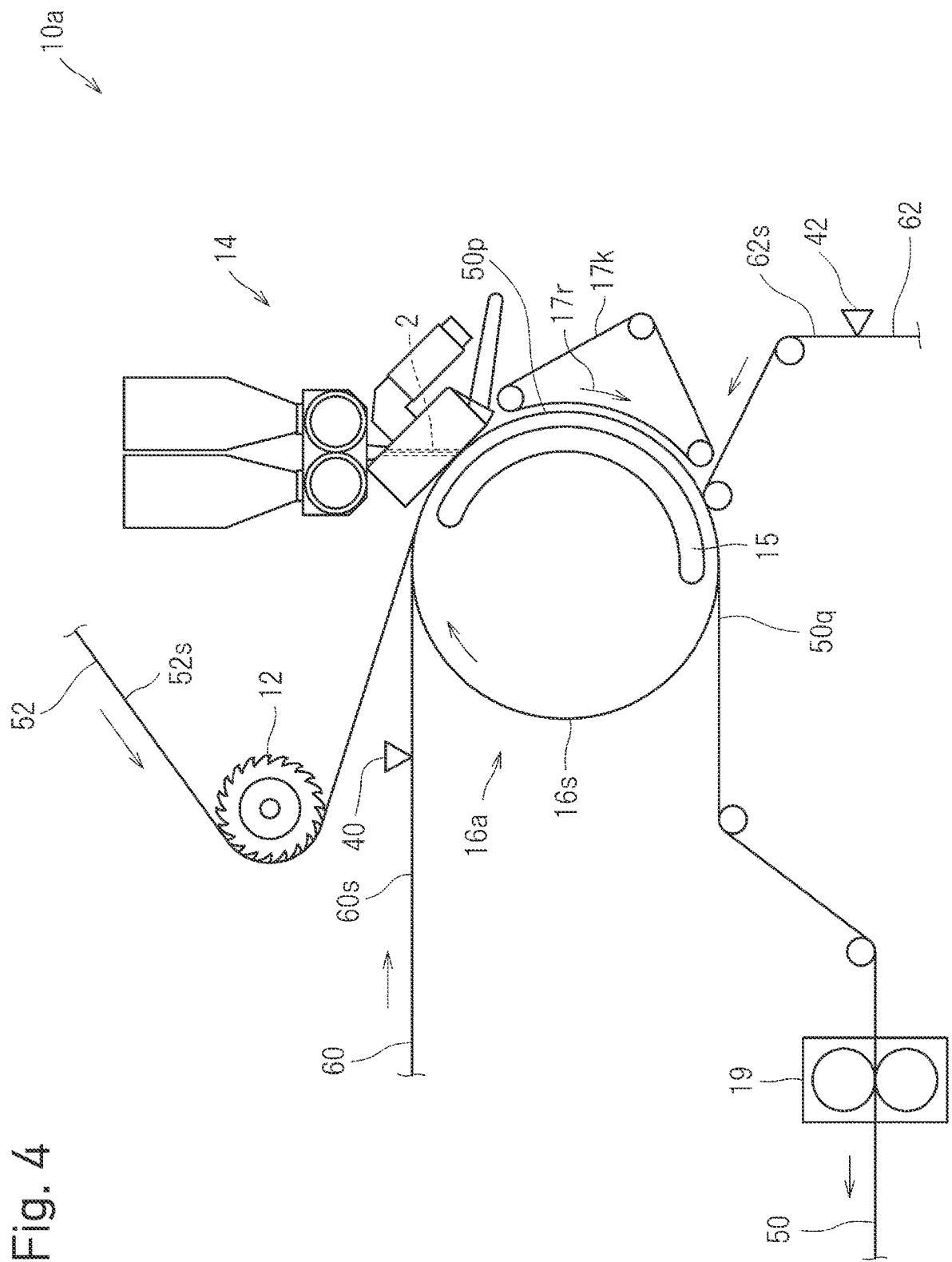
FIG. 4 is a schematic view of an absorbent body producing apparatus (first modification).

<First modification> FIG. 4 is a schematic view of an absorbent body producing apparatus 10a of the first modification in which the pressure difference increasing means is a belt-like member. As shown in FIG. 4, the absorbent body producing apparatus 10a is structured substantially similarly to the absorbent body producing apparatus 10 used in the first embodiment. Hereinafter, differences from the first embodiment will be mainly described, and parts of the same structure as those of the first embodiment are denoted by the same reference numerals.

As in the first embodiment, after a first adhesive such as hot melt adhesive is applied to the one main surface 60s by the first applying device 40 in such a manner that the breathability is maintained, the base sheet 60 is wound on the breathable cylindrical conveyance surface 16s of a first conveying device 16a. After the one main surface 52s side is napped by the napping device 12, the fiber sheet 52 is overlaid on the one main surface 60s of the base sheet 60 where the first adhesive is applied. This forms the first lamination body 50p. In the first lamination body 50p, the absorbent substance 2 supplied from the spraying device 14 is sprayed onto the one main surface 52s of the fiber sheet 52.

Inside the first conveying device 16a, a vacuum box 15 is provided so that the base sheet 60 is sucked through the conveyance surface 16s over the entire section where the base sheet 60 is wound. Unlike the first embodiment, the suction section is the entire section where the base sheet 60 is wound on the conveyance surface 16s, and the absorbent substance 2 is sprayed in the middle of the suction section.

After a second adhesive such as hot melt adhesive is applied onto the one main surface 62s by the second applying device 42, the cover sheet 62 is overlaid on the one main surface 52s of the fiber sheet 52 of the first lamination body 50p sprayed with the absorbent substance 2. This forms the second lamination body 50q. Unlike the first embodiment, no second conveying device 18 is provided, and the cover sheet 62 and the second lamination body 50q are conveyed by the first conveying device 16a.

The second lamination body 50q is discharged from the first conveying device 16a and is then compressed in the thickness direction by the compressing device 19, so that the first and second adhesives diffuse into the fiber sheet 52. This forms the continuous absorbent body 50 where the absorbent substance 2 is fixed.

Unlike that of the first embodiment, the pressure difference increasing means is a member 17k in the form of a belt (hereinafter referred to as belt-like member 17k). The belt-like member 17k is a breathable endless belt, and is structured so as to circulate in the direction indicated by the arrow 17r. For example, the belt-like member 17k is formed so as to have a mesh structure or the like, or through holes, slits or the like are formed on the belt-like member 17k.

While the belt-like member 17k and the fiber sheet 52 of the first lamination body 50p wound on the conveyance surface 16s of the first conveying device 16a are shown as being separated from each other in FIG. 4, the belt-like member 17k moves together with the fiber sheet 52 while being in contact with the one main surface 52s of the fiber sheet 52 sprayed with the absorbent substance 2. That is, the first lamination body 50p where the fiber sheet 52 and the base sheet 60 are laminated is conveyed while being sandwiched between the conveyance surface 16s and the belt-like member 17k and at this time, is sucked through the conveyance surface 16s so that air flows from the belt-like member 17k side to the conveyance surface 16s side.

By appropriately structuring the belt-like member 17k, the air flow penetrating the fiber sheet 52 to move toward the conveyance surface 16s is suppressed, so that the pressure difference between the conveyance surface 16s side and the opposite side of the fiber sheet 52 can be made large. By doing this, the absorbent body 50 can be produced in which a larger amount of granular absorbent substance 2 is caused to penetrate into the inside of the fiber sheet 52 from the napped one main surface 52s of the fiber sheet 52 and rewet is less likely to occur.

Figure 5:
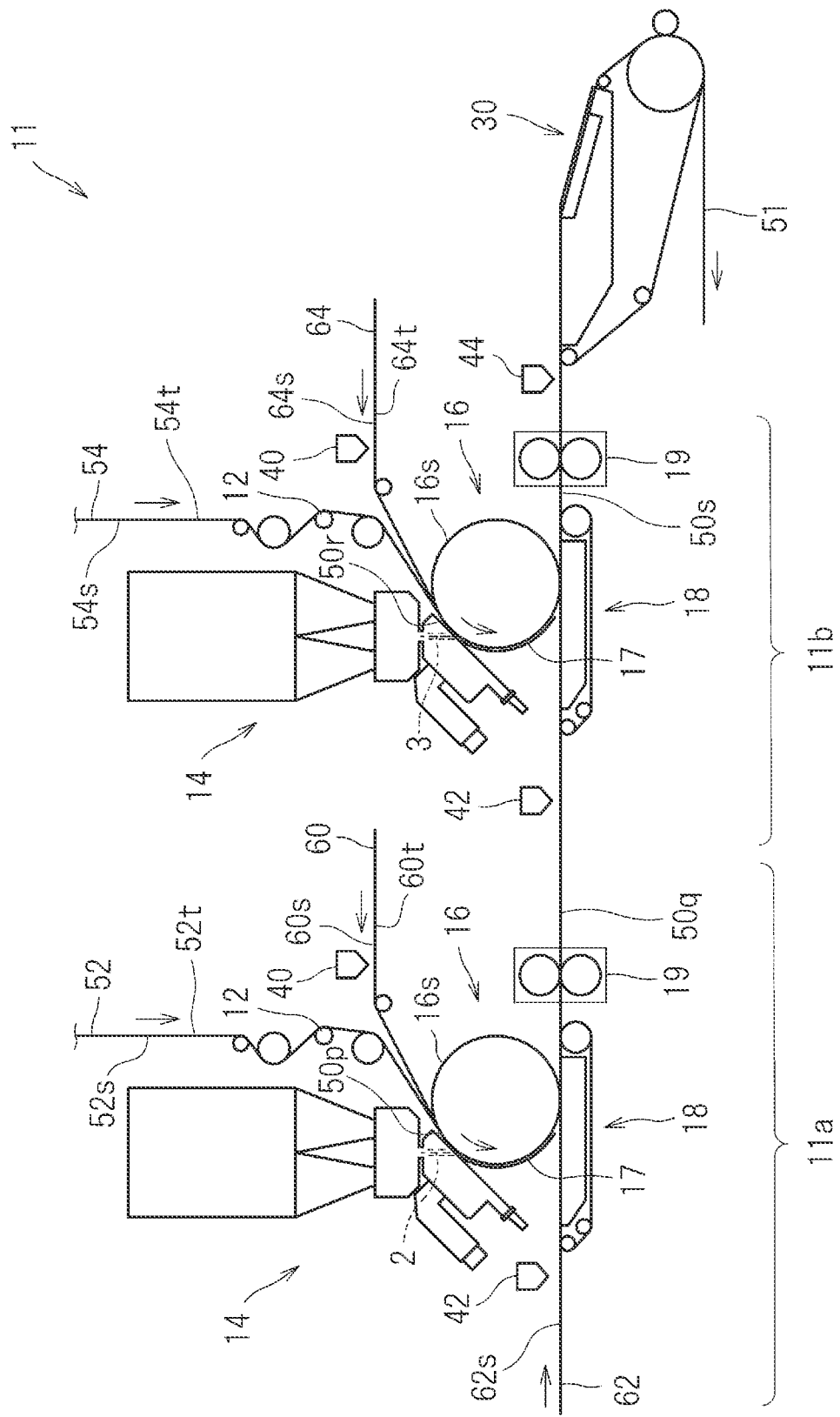
FIG. 5 is a schematic view of an absorbent body producing apparatus (second embodiment).
Figure 6:
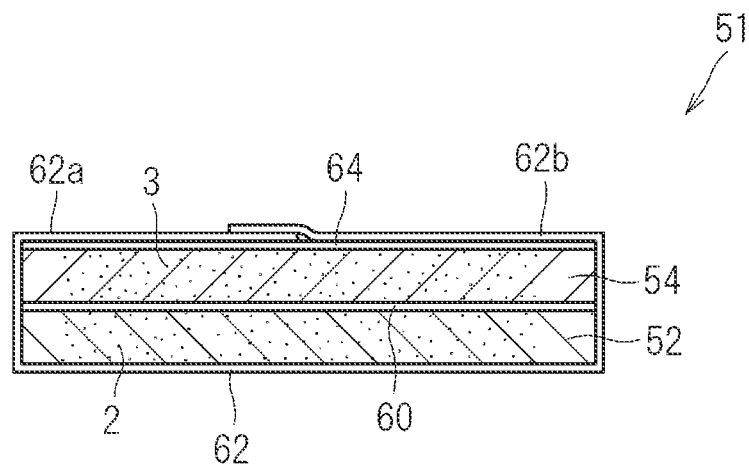
FIGS. 6A and 6B are schematic views of an absorbent body (second embodiment).
Figure 6:
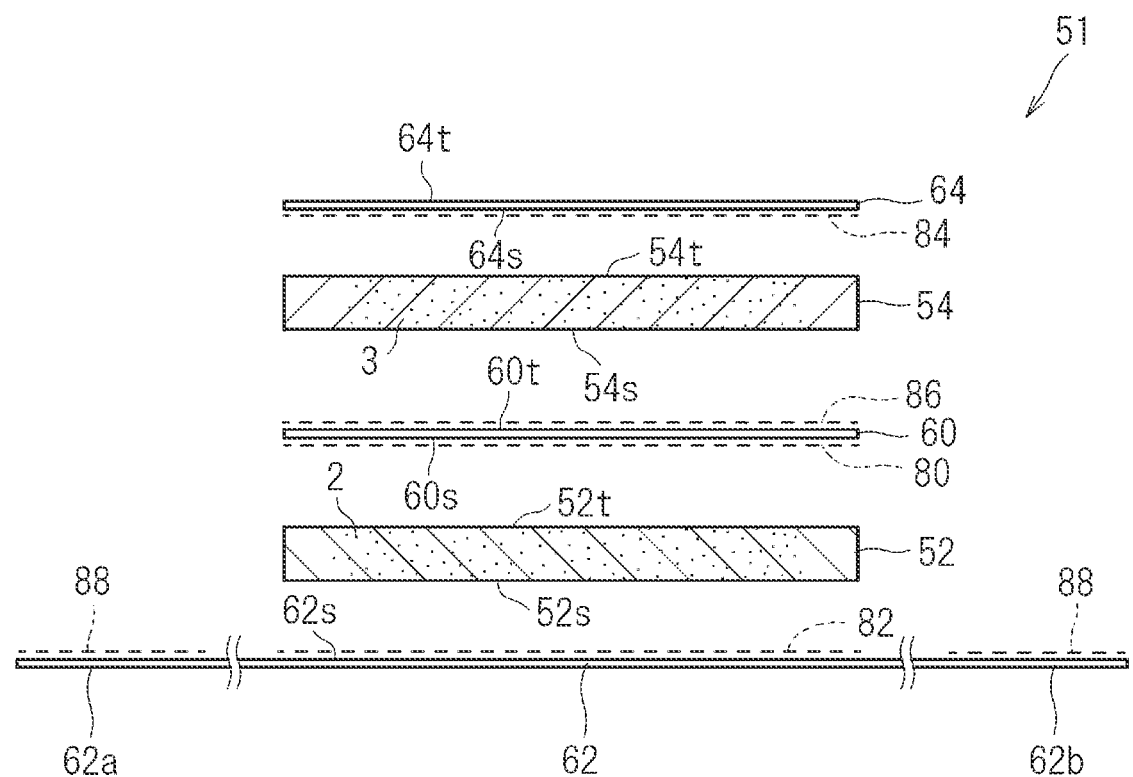
Figure 7:
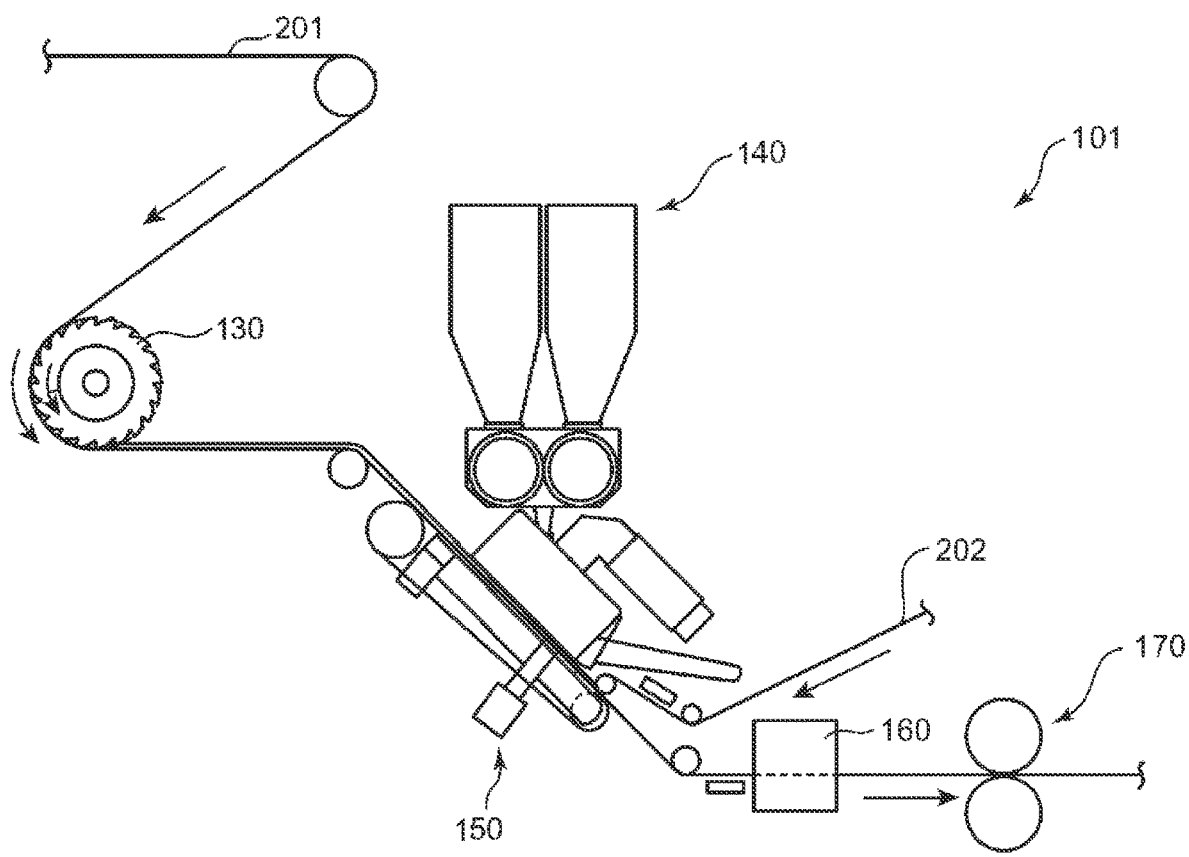
FIG. 7 is a schematic view of the absorbent body producing apparatus (conventional example).

<Second embodiment> A second embodiment in which an absorbent body 51 including two layers of fiber sheets 52 and 54 is produced will be described with reference to FIGS. 5, 6A and 6B. FIG. 5 is a schematic view of an absorbent body producing apparatus 11 used in the second embodiment. FIGS. 6A and 6B are schematic views of the absorbent body 51 cut vertically to a conveyance direction. FIG. 6A is an assembled view, and FIG. 6B is a disassembled view.

As shown in FIG. 5, the absorbent body producing apparatus 11 is provided with: first and second apparatuses 11a and 11b having the same structure as the absorbent body producing apparatus 10 of the first embodiment; a third applying device 44; and a folding device 30.

The first apparatus 11a continuously produces, as in the first embodiment, the second lamination body 50q in which the continuous base sheet 60 (hereinafter, referred to also as intermediate sheet 60), the continuous fiber sheet 52 and the continuous cover sheet 62 are laminated. The second lamination body 50q is compressed in the thickness direction by the compressing device 19.

The second apparatus 11b continuously produces, substantially as in the first embodiment, a fourth lamination body 50s in which a continuous other base sheet 64, a continuous other fiber sheet 54 and the continuous second lamination body 50q are laminated. The fourth lamination body 50s is compressed in the thickness direction by the compressing device 19.

Specifically, in the second apparatus 11b, the other fiber sheet 54 has one main surface 54s side thereof napped by the napping device 12 before supplied to the first conveying device 16. The other base sheet 64 has breathability, and before it is supplied to the first conveying device 16, a third adhesive 84 such as hot melt adhesive (see FIG. 6) is applied to one main surface 64s by the first applying device 40 in such a manner that the breathability is maintained. The other main surface 64t of the other base sheet 64 is sucked through the conveyance surface 16s of the first conveying device 16. The other main surface 54t of the other fiber sheet 54 and the one main surface 64s of the other base sheet 64 are overlaid on each other to form a third lamination body 50r where the other fiber sheet 54 is laminated on the other base sheet 64.

In the second lamination body 50q formed by the first apparatus 11a, after a fourth adhesive 86 such as hot melt adhesive (see FIG. 6B) is applied to the other main surface 60t of the intermediate sheet 60 of the second lamination body 50q by the second applying device 42, the other main surface 60t of the intermediate sheet 60 of the second lamination body 50q is overlaid on the one main surface 54s of the other fiber sheet 54 of the third lamination body 50r. This forms the fourth lamination body 50s where the second lamination body 50q is laminated on the third lamination body 50r.

As shown in FIGS. 6A and 6B, the cover sheet 62 is larger in the dimension in the width direction (a direction vertical to the conveyance direction and the thickness direction) than the other sheets 52, 54, 60 and 64, and is laminated so as to protrude from both sides in the width direction of the other sheets 52, 54, 60 and 64.

As shown in FIGS. 5, 6A and 6B, in the third applying device 44, a fifth adhesive 88 such as hot melt adhesive is applied to the one main surface 62s of parts 62a and 62b on both sides in the width direction of the cover sheet 62. The folding device 30 folds the parts 62a and 62b on both sides in the width direction of the cover sheet 62 where the fifth adhesive 88 is applied and overlays them on the other base sheet 64. This forms the continuous absorbent body 51 structured so as to be wrapped with the cover sheet 62.

As shown in FIGS. 6A and 6B, in the absorbent body 51, the one main surface 60s of the intermediate sheet 60 and the other main surface 52t of the fiber sheet 52 are bonded together by the first adhesive 80 and the one main surface 62s of the cover sheet 62 and the one main surface 52s of the fiber sheet 52 are bonded together by the second adhesive 82. Moreover, the one main surface 64s of the other base sheet 64 and the other main surface 54t of the other fiber sheet 54 are bonded together by the third adhesive 84, and the other main surface 60t of the intermediate sheet 60 and the one main surface 54s of the other fiber sheet 54 are bonded together by the fourth adhesive 86. The one main surface 62s of parts 62a and 62b on both sides in the width direction of the cover sheet 62 and the other main surface 64t of the other base sheet 64 are bonded together by the fifth adhesive 88. The absorbent substance 2 is disposed inside the fiber sheet 52, and an other absorbent substance 3 is disposed inside the other fiber sheet 54. While it is preferable to use the same adhesive as the first to fifth adhesives 80, 82, 84, 86 and 88, adhesives different in ingredients may be used.

When an absorbent article is formed by using the absorbent body 51, it is preferable to dispose the one main surfaces 52s and 54s of the fiber sheets 52 and 54 on the skin surface side and dispose the other main surfaces 52*t* and 54*t* thereof on the non-skin surface side as in the first embodiment.

<Summary> As described above, the absorbent bodies 50 and 51 can be produced in which a larger amount of granular absorbent substances 2 and 3 are caused to penetrate into the inside of the fiber sheets 52 and 54 from the napped one main surfaces 52*s* and 54*s* of the fiber sheets 52 and 54 and rewet is less likely to occur.

The present invention is not limited to the above-described embodiments and may be variously modified when carried out.

For example, while a case is shown in which the other main surface side of the fiber sheet is sucked through the cylindrical conveyance surface of the conveying device, the conveyance surface of the conveying device may be structured appropriately; for example, the conveyance surface of the conveying device may be planar.

DESCRIPTION OF REFERENCE NUMERALS

2, 3 Absorbent substance
16, 16*a* First conveying device (conveying device)
16*k* Suction section
16*s* Conveyance surface
17 Plate member (pressure difference increasing means)
17*k* Belt-like member (pressure difference increasing means)
17*p* Through hole (airflow passage)
17*s*, 17*t* Main surface
50, 51 Absorbent body
52, 54 Fiber sheet
52*s*, 54*s* One main surface
52*t*, 54*t* Other main surface
62 Cover sheet

The invention claimed is:

1. An absorbent body producing method, comprising:
a first step in which a fiber sheet having one main surface side thereof napped is supplied to a conveying device and conveyed while an other main surface side of the fiber sheet is being sucked through a conveyance surface of the conveying device; and
a second step in which a granular absorbent substance capable of absorbing and holding liquid is sprayed onto the napped one main surface of the fiber sheet so that the granular absorbent substance is disposed only in a single suction section where air is continuously sucked through the other main surface of the fiber sheet and the conveyance surface and the sprayed absorbent substance is caused to penetrate into an inside of the fiber sheet only in the single suction section,
wherein at the first and second steps, a pressure difference increasing means is provided that faces the one main surface of the fiber sheet sprayed with the absorbent substance and being conveyed in the suction section and that suppresses an air flow penetrating the fiber sheet to move inward from the conveyance surface to thereby increase the pressure difference between the conveyance surface side and the opposite side of the fiber sheet.

2. The absorbent body producing method according to claim 1,
wherein the pressure difference increasing means is a plate-like or belt-like member having one main surface and an other main surface opposite to each other, and
the one main surface of the member faces the one main surface of the fiber sheet sprayed with the absorbent substance and being conveyed in the suction section.

3. The absorbent body producing method according to claim 2, further comprising:
a third step in which an adhesive is applied to one main surface of a cover sheet; and
a fourth step in which the one main surface of the cover sheet where the adhesive is applied is overlaid on the one main surface of the fiber sheet sprayed with the absorbent substance to laminate the cover sheet on the fiber sheet.

4. The absorbent body producing method according to claim 2,
wherein in the member,
an opening is formed on the one main surface of the member, and
an airflow passage communicating with the opening is formed.

5. The absorbent body producing method according to claim 4, further comprising:
a third step in which an adhesive is applied to one main surface of a cover sheet; and
a fourth step in which the one main surface of the cover sheet where the adhesive is applied is overlaid on the one main surface of the fiber sheet sprayed with the absorbent substance to laminate the cover sheet on the fiber sheet.

6. The absorbent body producing method according to claim 4,
wherein the airflow passage is a through hole passing through between the one main surface and the other main surface of the member, and
a plurality of the through holes are formed on the member.

7. The absorbent body producing method according to claim 6, further comprising:
a third step in which an adhesive is applied to one main surface of a cover sheet; and
a fourth step in which the one main surface of the cover sheet where the adhesive is applied is overlaid on the one main surface of the fiber sheet sprayed with the absorbent substance to laminate the cover sheet on the fiber sheet.

8. The absorbent body producing method according to claim 1, further comprising:
a third step in which an adhesive is applied to one main surface of a cover sheet; and
a fourth step in which the one main surface of the cover sheet where the adhesive is applied is overlaid on the one main surface of the fiber sheet sprayed with the absorbent substance to laminate the cover sheet on the fiber sheet.

9. The absorbent body producing method according to claim 1, wherein the air is sucked inwardly in the suction section through a mesh structure of the conveyance surface of the conveying device by a vacuum chamber in the conveying device.

10. The absorbent body producing method according to claim 9, wherein in the suction section, the pressure difference increasing means forms, on the fiber sheet, first facing areas where the air flow sucked is weak and second facing areas where the air flow sucked is stronger than the first facing areas, the first facing areas and the second facing areas changing alternately.

11. The absorbent body producing method according to claim 9, wherein the air is sucked between a first position where a base sheet has moved by a predetermined distance after being wound on the conveyance surface and a second position where the base sheet separates from the conveyance surface.

\* \* \* \* \*